（12）United States Patent
Mergens

(10) Patent No.: US 10,842,684 B2
(45) Date of Patent: Nov. 24, 2020

(54) REUSABLE SHIELD AND LINER FOR USE DURING MENSTRUATION

(71) Applicant: Days for Girls International, Lynden, WA (US)

(72) Inventor: Celeste Mergens, Lynden, WA (US)

(73) Assignee: DAYS FOR GIRLS INTERNATIONAL, Lynden, WA (US)

( * ) Notice: Subject to any disclaimer, the term of this patent is extended or adjusted under 35 U.S.C. 154(b) by 206 days.

(21) Appl. No.: 15/207,402

(22) Filed: Jul. 11, 2016

(65) Prior Publication Data

US 2016/0317361 A1    Nov. 3, 2016

Related U.S. Application Data

(63) Continuation-in-part of application No. 14/445,301, filed on Jul. 29, 2014, now Pat. No. 9,877,878.

(51) Int. Cl.
| | |
|---|---|
| A61F 13/15 | (2006.01) |
| A61F 13/20 | (2006.01) |
| A61F 13/56 | (2006.01) |
| A61F 13/472 | (2006.01) |
| A61L 15/26 | (2006.01) |
| A61L 15/52 | (2006.01) |
| A61F 13/49 | (2006.01) |
| A61F 13/505 | (2006.01) |

(52) U.S. Cl.
CPC ...... *A61F 13/15268* (2013.01); *A61F 13/472* (2013.01); *A61F 13/49003* (2013.01); *A61F 13/505* (2013.01); *A61F 13/5605* (2013.01); *A61L 15/26* (2013.01); *A61L 15/52* (2013.01); *A61F 2013/15276* (2013.01); *A61F 2013/16* (2013.01)

(58) Field of Classification Search
CPC .......... A61F 13/15268; A61F 13/49003; A61F 13/5605; A61F 2013/15276; A61F 2013/16; A61F 13/472; A61F 13/505; A61L 15/52
See application file for complete search history.

(56) References Cited

U.S. PATENT DOCUMENTS

| | | | | | |
|---|---|---|---|---|---|
| 1,695,153 | A | * | 12/1928 | Nelson | A61F 13/64 604/397 |
| 1,992,075 | A | * | 2/1935 | Kennard | A61F 13/505 604/397 |
| 2,494,307 | A | * | 1/1950 | Niolon | A61F 13/49003 604/385.15 |
| 2,571,357 | A | * | 10/1951 | Gemora | A61F 13/64 604/397 |
| 2,684,677 | A | * | 7/1954 | Pinney | A61F 13/49003 604/385.15 |
| 2,840,078 | A | * | 6/1958 | Smith | A61F 13/64 604/397 |
| 3,117,577 | A | * | 1/1964 | Mosier | A61F 13/64 604/399 |
| 3,225,765 | A | * | 12/1965 | Mosier | A61F 13/64 604/397 |

(Continued)

*Primary Examiner* — Michele M Kidwell
(74) *Attorney, Agent, or Firm* — DLA Piper LLP (US)

(57) ABSTRACT

A reusable shield and liner for use by a woman during menstruation is disclosed. The liner has a predetermined shape and comprises two or more layers. The predetermined shape can be an octagon, a circle, or an oral. The shield contains one water-resistant layer.

17 Claims, 10 Drawing Sheets

(56) References Cited

U.S. PATENT DOCUMENTS

| | | | | |
|---|---|---|---|---|
| 3,489,149 A * | 1/1970 | Larson | A61F 13/72 | 604/372 |
| 4,044,769 A * | 8/1977 | Papajohn | A61F 13/72 | 604/385.19 |
| 4,664,663 A * | 5/1987 | Brier | A61F 13/47 | 604/387 |
| 5,181,915 A * | 1/1993 | Smith | A61F 13/49004 | 604/358 |
| 5,360,422 A * | 11/1994 | Brownlee | A61F 13/505 | 604/385.14 |
| 5,429,627 A * | 7/1995 | Johnson | A61F 13/15268 | 270/41 |
| 5,752,946 A * | 5/1998 | Boberg | A61F 13/47 | 604/373 |
| 5,814,037 A * | 9/1998 | Coates | A61F 13/49004 | 604/385.15 |
| 6,042,575 A * | 3/2000 | Osborn, III | A61F 13/15203 | 604/385.23 |
| 6,443,933 B1 * | 9/2002 | Suzuki | A61F 13/4942 | 604/358 |
| 6,764,477 B1 * | 7/2004 | Chen | A61F 13/4702 | 604/385.14 |
| 7,166,095 B1 * | 1/2007 | Coates | A61F 13/495 | 604/385.14 |
| 8,894,626 B2 * | 11/2014 | Beck | A61F 13/505 | 604/385.01 |
| 8,968,264 B2 * | 3/2015 | Coates | A61F 13/49 | 604/385.14 |
| 9,011,403 B2 * | 4/2015 | De Bruin | A61F 13/4906 | 604/385.14 |
| 9,820,893 B2 * | 11/2017 | Marquette | A61L 15/28 | |
| 9,877,878 B2 * | 1/2018 | Rescorl | A61F 13/49003 | |
| 2001/0034510 A1 * | 10/2001 | Shinkai | A61F 13/15211 | 604/385.01 |
| 2003/0216705 A1 * | 11/2003 | Coates | A61F 13/495 | 604/386 |
| 2004/0158225 A1 * | 8/2004 | Coates | A61F 13/495 | 604/397 |
| 2004/0236298 A1 * | 11/2004 | Coates | A61F 13/476 | 604/385.04 |
| 2005/0256497 A1 * | 11/2005 | Gottwald | A61F 13/74 | 604/386 |
| 2006/0224136 A1 * | 10/2006 | Martinez | A61F 13/472 | 604/385.15 |
| 2008/0009818 A1 * | 1/2008 | Rubio | A61F 13/474 | 604/385.16 |
| 2008/0021433 A1 * | 1/2008 | Allison-Rogers | A61F 13/5616 | 604/397 |
| 2008/0108964 A1 * | 5/2008 | Edwall | A61F 13/49011 | 604/385.3 |
| 2009/0299313 A1 * | 12/2009 | Knightingale | A61F 13/15268 | 604/367 |
| 2010/0168709 A1 * | 7/2010 | Hodgkin | A61F 13/49004 | 604/385.14 |
| 2010/0318057 A1 * | 12/2010 | Yakem | A61F 13/495 | 604/396 |
| 2011/0015600 A1 * | 1/2011 | Pham | A61F 13/505 | 604/367 |
| 2011/0178492 A1 * | 7/2011 | Coates | A61F 13/505 | 604/385.101 |
| 2012/0029459 A1 * | 2/2012 | Hallouin | A61F 13/49413 | 604/385.15 |
| 2012/0109092 A1 * | 5/2012 | Austin | A61F 13/505 | 604/385.03 |
| 2013/0023846 A1 * | 1/2013 | Beck | A61F 13/505 | 604/385.14 |
| 2013/0172844 A1 * | 7/2013 | Coates | A61F 13/505 | 604/385.14 |
| 2014/0114273 A1 * | 4/2014 | Sierra | A61F 13/74 | 604/397 |

* cited by examiner

REUSABLE SHIELD AND LINER FOR USE DURING MENSTRUATION

CROSS-REFERENCE TO RELATED APPLICATIONS

This application is a Continuation-in-Part application of U.S. patent application Ser. No. 14/445,301, filed on Jul. 29, 2014 and entitled "REUSABLE SHIELD AND LINER FOR USE DURING MENSTRUATION," which is hereby incorporated herein by reference in its entirety.

TECHNICAL FIELD

A reusable shield and liner for use by a woman during menstruation is disclosed.

BACKGROUND OF THE INVENTION

In many developing countries, women do not have access to affordable menstruation supplies. Women often are chastised and isolated during the menstruation process, and in some countries, it is customary for women to miss school or work during the menstruation process.

What is needed is an affordable, reusable device to assist women during the menstruation process.

SUMMARY OF THE INVENTION

A reusable shield and liner for use by a woman during menstruation is disclosed.

In one aspect, provided herein is a reusable liner and shield that comprises a liner and a shield. The liner comprises one or more layers of cloth of a predetermined shape selected from the group consisting of an octagon, a circle, and an oval. The shield comprises a first piece; a second piece attached to a first side of the first piece to form a first pocket; a third piece attached to the first side of the first piece to form a second pocket; and a fourth piece attached to a second side of the first piece. For use, one end of the liner is placed in the first pocket and another end of the liner is placed in the second pocket.

In some embodiments, the fourth piece is made of polyurethane laminate.

In some embodiments, the cloth comprises cotton, flannel, or synthetic material.

In some embodiments, the first piece, second piece, and third piece each comprise cotton.

In some embodiments, the shield comprises a fifth piece attached to the fourth piece. In some embodiments, fifth piece comprises cotton.

In some embodiments, the shield further comprises an attachment mechanism. In some embodiments, the attachment mechanism comprises one selected from the group consisting of a snap, a button, Velcro, zipper, and a pair of strings for forming a knot.

In another aspect, the reusable liner and shield provided herein including a liner comprising one or more layers of cloth and a shield that comprises: a first piece; a second piece attached to a first side of the first piece to form a first pocket; a third piece attached to the first side of the first piece to form a second pocket; and a fourth piece attached to a second side of the first piece. Each layer of cloth in the layer comprises a more absorbent center region flanked by two side regions. For use, one end of the liner is placed in the first pocket and another end of the liner is placed in the second pocket.

In some embodiments, the center region is made of cotton, flannel, or a synthetic absorbent material. In some embodiments, the center region is padded. In some embodiments, the center region is formed with more layers of multiple than the side regions.

In another aspect, provided herein is a method of using a reusable liner and shield, that comprises the steps of: folding an octagonal liner along a first fold line; folding the octagonal liner along a second fold line to form a rectangle; inserting one end of the liner into a first pocket in a shield; inserting another end of the liner into a second pocket in a shield; attaching the shield to an undergarment using an attachment mechanism; and removing the liner from the shield.

In some embodiments, the liner comprises a first layer and a second layer. In some embodiments, the shield comprises a piece of polyurethane laminate. In some embodiments, the shield comprises a first piece of cotton attached to a first side of the piece of polyurethane laminate. In some embodiments, the shield comprises a second piece of cotton attached to a second side of the piece of polyurethane laminate. In some embodiments, the attachment mechanism comprises one selected from the group consisting of a snap, a button, Velcro, zipper, and a pair of strings for forming a knot.

In some embodiments, the method further comprises the step of washing the liner. In some embodiments, the method further comprises the step of reusing the liner in the shield.

One of skill in the art would understand that any embodiments of liner can be used in combination with any embodiment of shield.

DETAILED DESCRIPTION OF THE PREFERRED EMBODIMENTS

Figure 1:
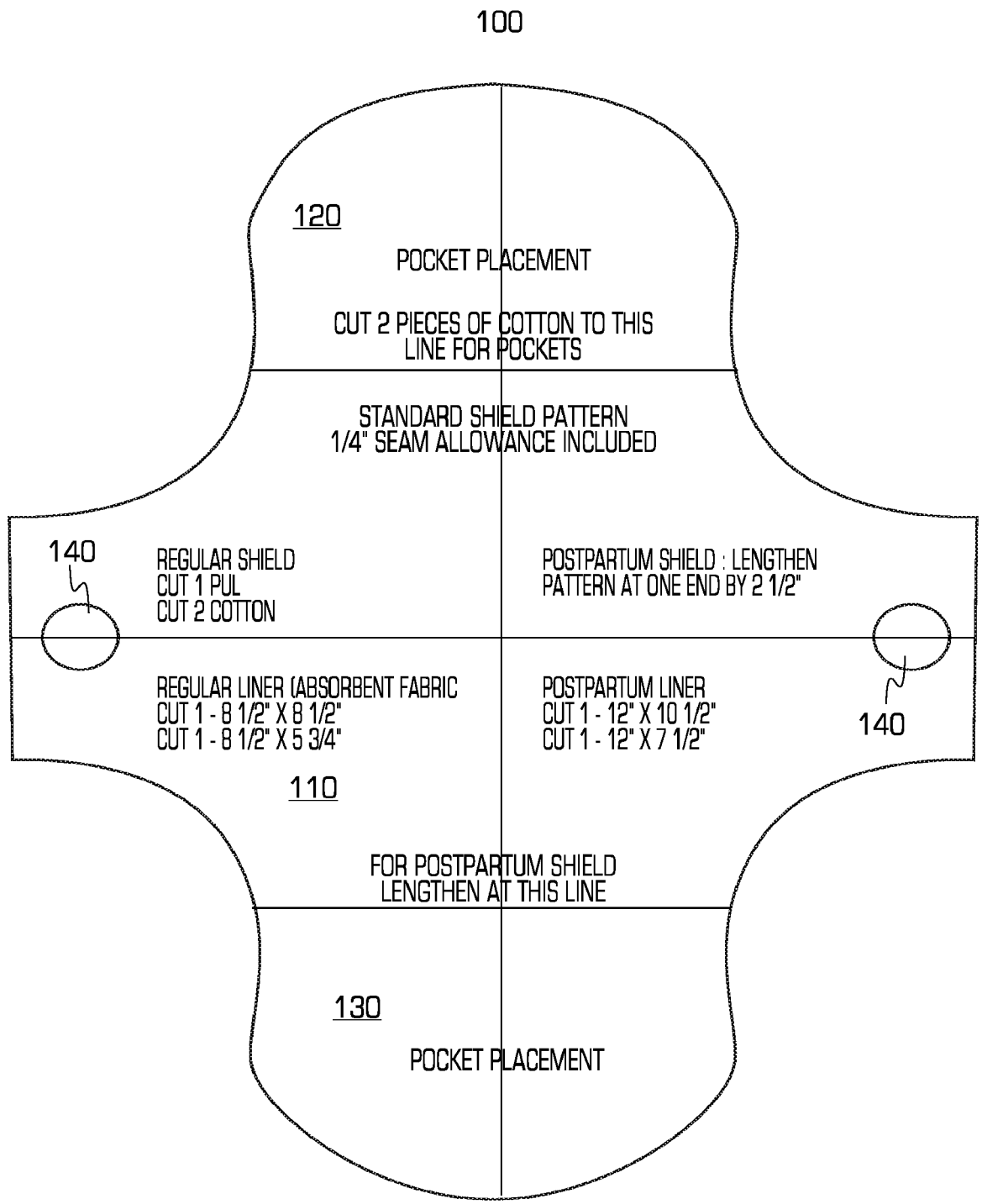
FIG. 1 depicts a prior art reusable shield developed by the applicant.

With reference to FIG. 1, prior art reusable shield 100 developed by the applicant is depicted. Shield 100 comprises a first piece 110 in the general shape shown in FIG. 1, a second piece 120 attached to the first piece 110 as shown, and a third piece 130 attached to the first piece as shown. First piece 110, second piece 120, and third piece 130 comprise pieces of cloth, preferably cotton. Second piece 120 and third piece 130 are sewn, adhered, or attached using other means to first piece 110 to form pockets. Shield 100 also comprises attachment mechanism 140, which can comprise a snap, button, Velcro, zipper, and one or more pairs of strings for forming a knot, or other known attachment mechanism.

Figure 2:
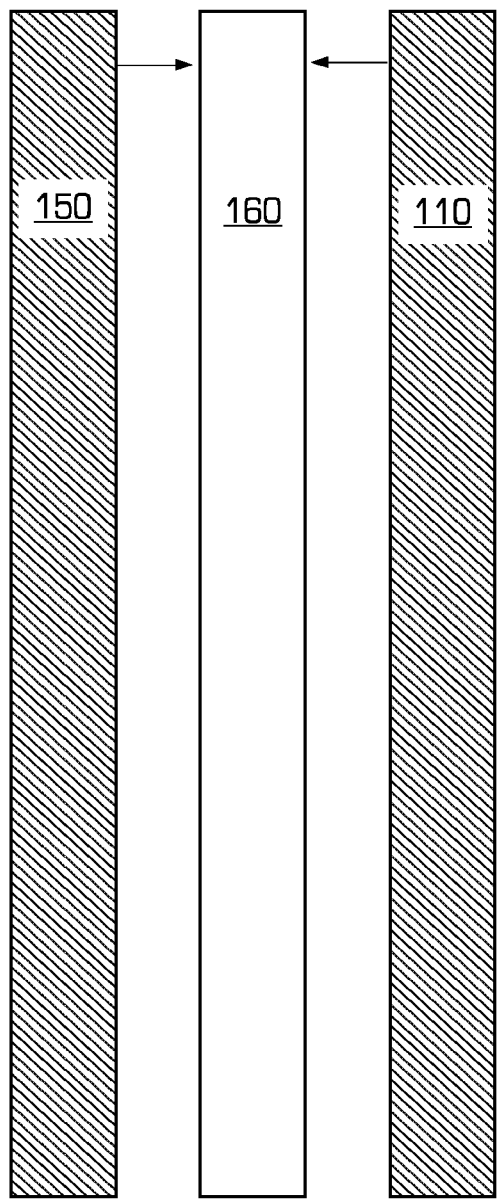
FIG. 2 depicts a side view of the prior art reusable shield of FIG. 1.

With reference to FIG. 2, first piece 110 also is attached to fourth piece 160, which is made of water-resistant material such as polyurethane laminate or other water-resistant material. Fourth piece 160 is of the same shape as first piece 110, and the side of first piece 110 opposite the side attached to second piece 120 and third piece 130 is sewn, adhered, or attached using other means to fourth piece 160. On the opposite site of fourth piece 160 is fifth piece 150, which can be identical to first piece 110. Fourth piece 160 and fifth piece 150 are sewn or adhered together or attached using other means. First piece 110, fourth piece 160, and fifth piece 150 can be sewn or adhered together or attached using other means in a contiguous manner.

Figure 3:
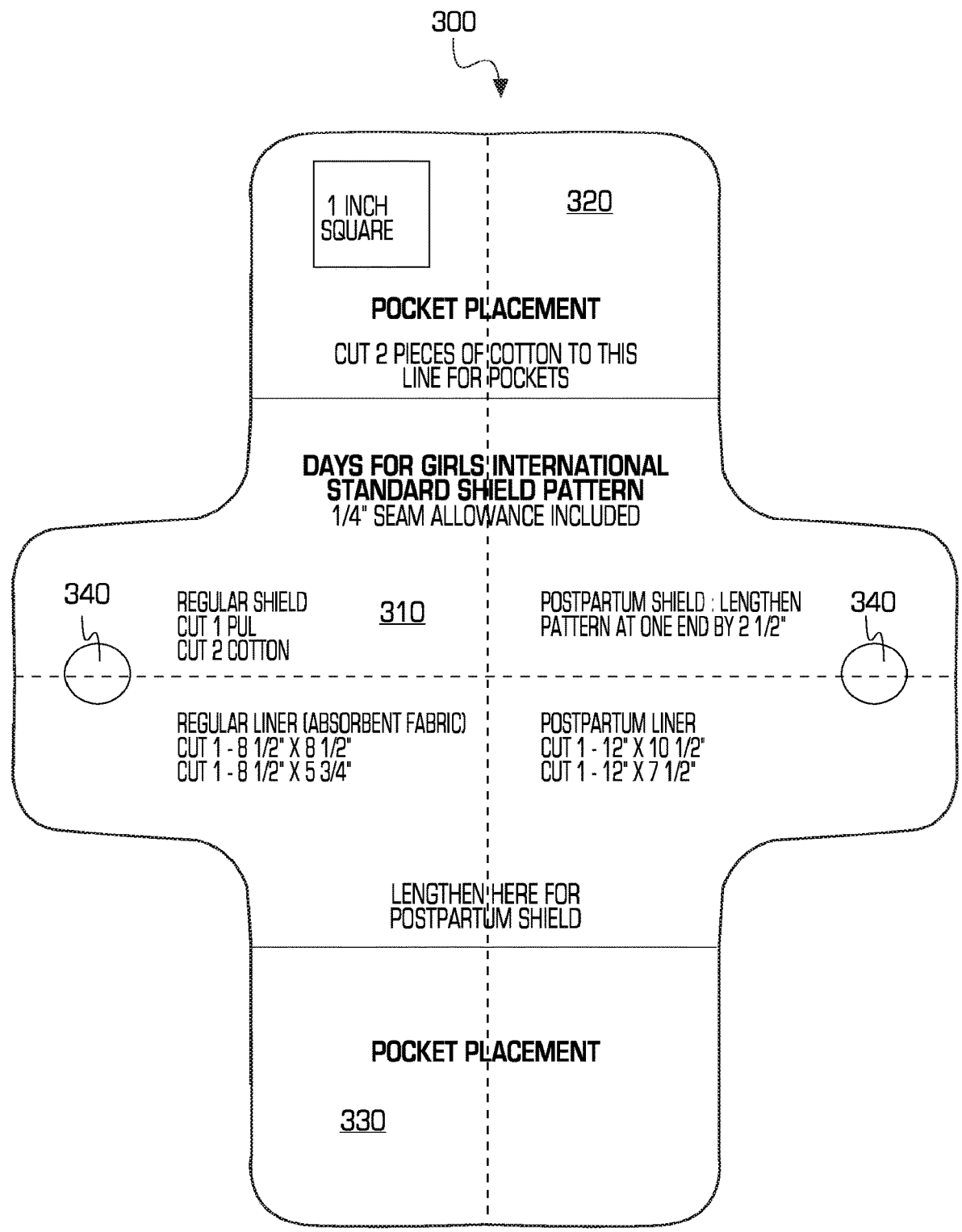
FIG. 3 depicts an embodiment of a reusable shield developed by the applicant.

With reference to FIG. 3, an embodiment of an improved reusable shield 300 is depicted. Shield 300 comprises a first piece 310 in the general shape shown in FIG. 3, a second piece 320 attached to the first piece 310 as shown, and a third piece 330 attached to the first piece as shown. First piece 310, second piece 320, and third piece 330 comprise pieces of cloth, preferably cotton. Second piece 320 and third piece 330 are sewn, adhered, or attached using other means to first piece 310 to form pockets. Shield 300 also comprises attachment mechanism 340, which can comprise a snap, button, Velcro, or other known attachment mechanism.

Figure 4:
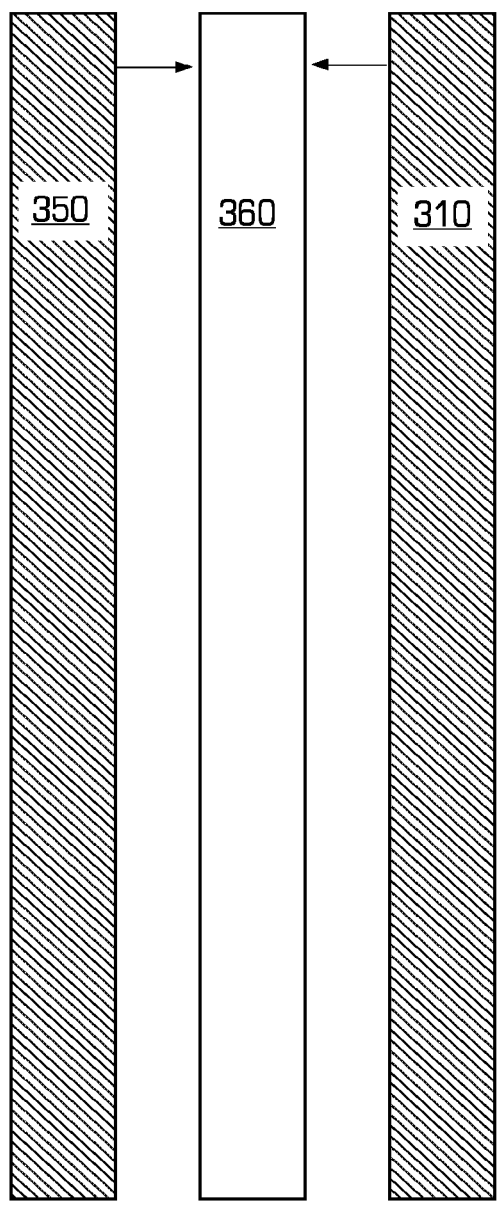
FIG. 4 depicts a side view of the reusable shield of FIG. 3.

With reference to FIG. 4, first piece 310 also is attached to fourth piece 360, which is made of water-resistant material such as polyurethane laminate or another water-resistant material. Fourth piece 360 is of the same shape as first piece 310, and the side of first piece 310 opposite the side attached to second piece 320 and third piece 330 is sewn, adhered, or attached using other means to fourth piece 360. On the opposite site of fourth piece 360 is fifth piece 350, which can be identical to first piece 310. Fourth piece 360 and fifth piece 350 are sewn or adhered together or attached using other means. First piece 310, fourth piece 360, and fifth piece 350 can be sewn or adhered together or attached using other means in a contiguous manner.

Figure 5:
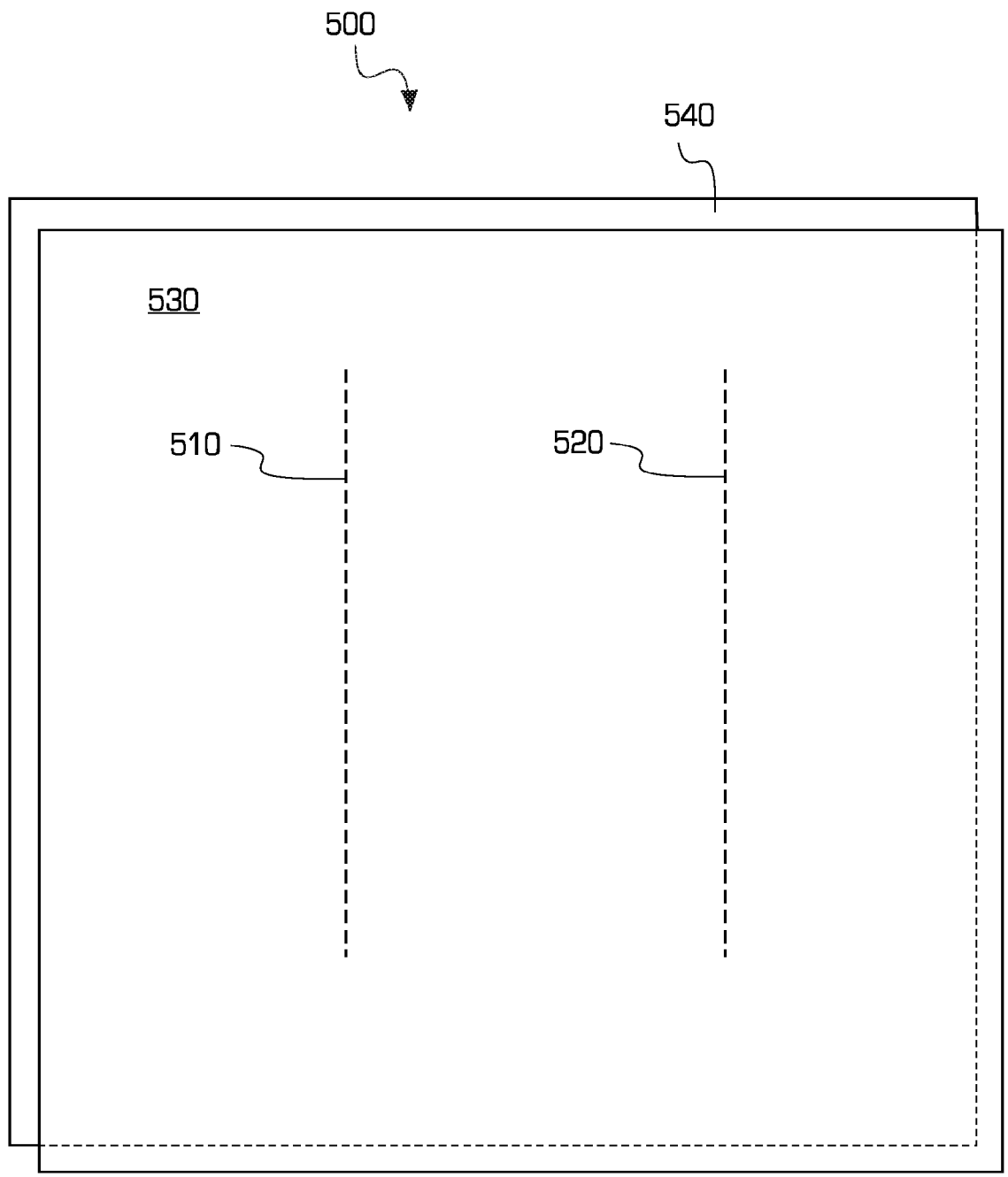
FIG. 5 depicts a prior art reusable liner developed by the applicant.

With reference to FIG. 5, prior art reusable liner 500 is depicted. Liner 500 has a generally square shape and can be folded along fold lines 510 and 520. Liner 500 comprises first layer 530, and optionally includes second layer 540 as well. First layer 530 and second layer 540 are made from cloth, preferably cotton or flannel. First layer 530 and second layer 540 are sewn or adhered together or attached using other means.

Figure 6:
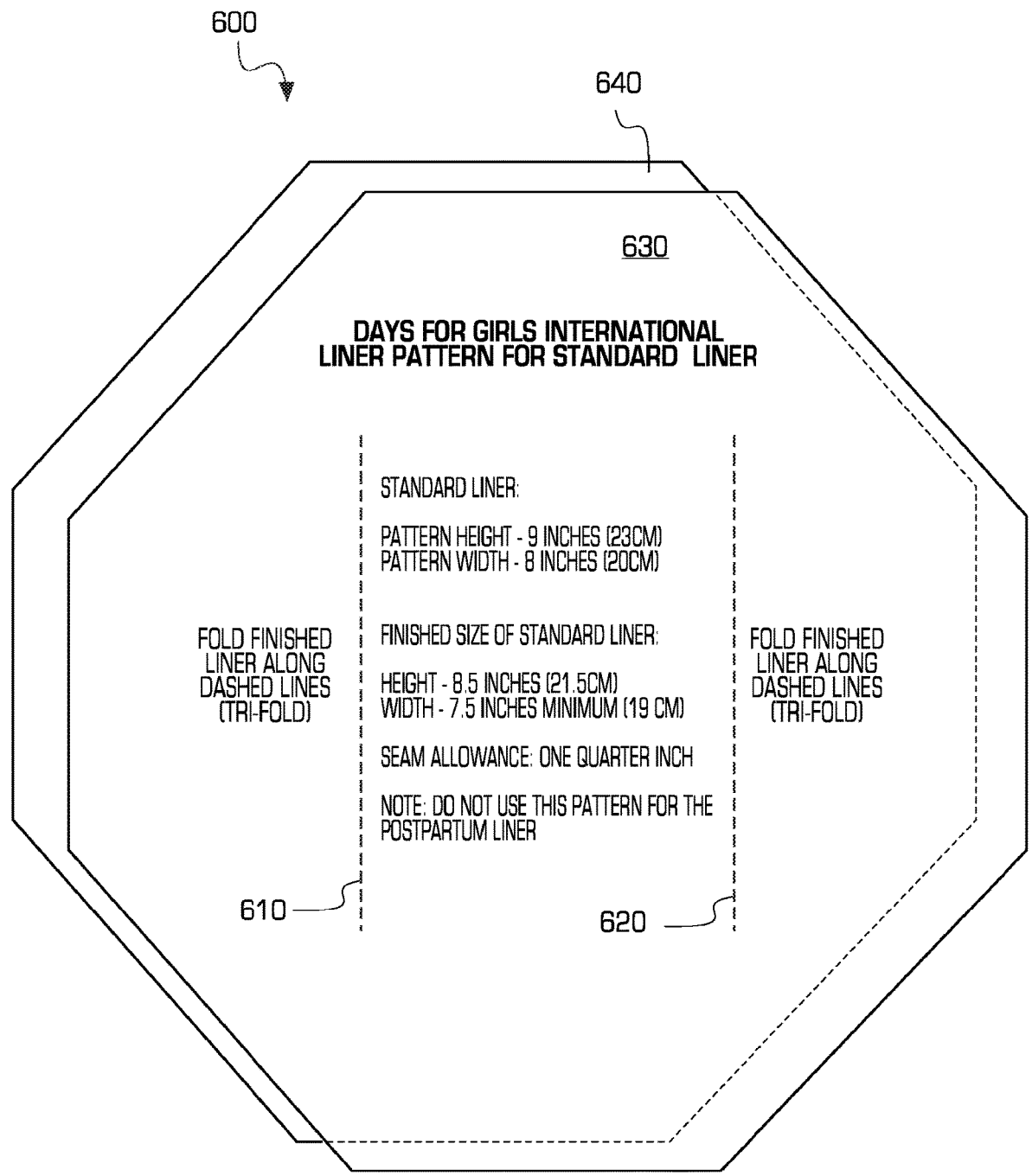
FIG. 6 depicts an embodiment of a reusable liner developed by the applicant.

With reference to FIG. 6, an embodiment of an improved liner 600 is depicted. Liner 600 has a generally octagonal shape and can be folded along fold lines 610 and 620. Liner 600 is an improvement over liner 500 because it is less bulky in certain areas and is more comfortable for a woman to wear. Liner 600 comprises first layer 630 and optionally includes second layer 640. First layer 630 and second layer 640 are made from cloth, preferably cotton or flannel. First layer 630 and second layer 640 are sewn or adhered together or attached using other means.

Figure 7:
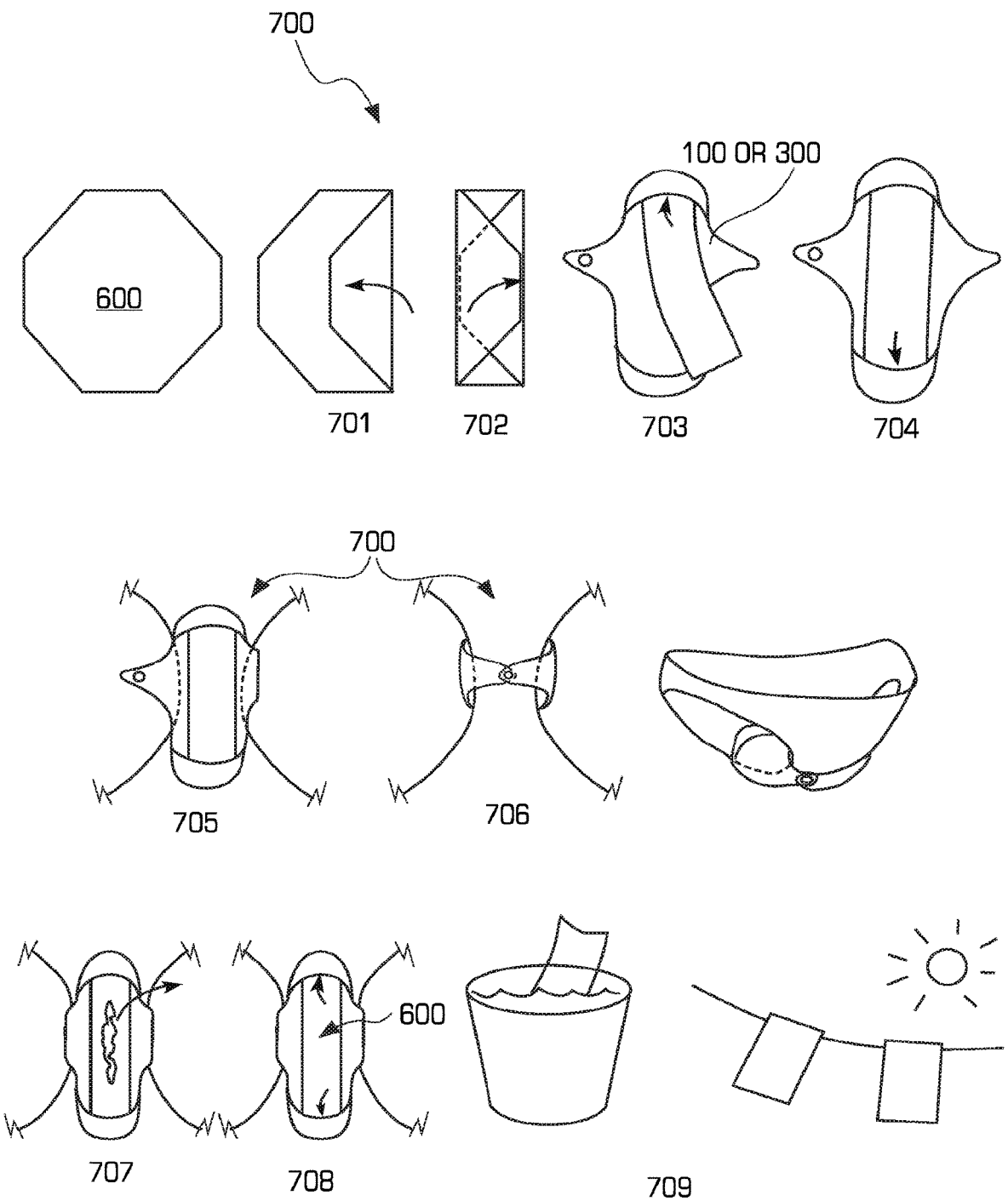
FIG. 7 depicts a method for assembling and using a shield and liner.

With reference to FIG. 7, a method 700 of using liner 600 in conjunction with shield 100 or shield 300 is shown. Liner 600 is folded along fold line 620 (step 701) and then is folded along fold line 610 (step 702) to create a generally rectangular shape. Liner 600 is then inserted into shield 100 (or shield 300) by inserting one end of liner 600 into the pocket formed by first piece 110 and second piece 120 (or first piece 310 and second piece 320) (step 703) and inserting the other end of liner 600 into the pocket formed by first piece 110 and third piece 130 (or first piece 310 and third piece 330) (step 704). Liner 600 and shield 100 or shield 300 are then attached to underwear 700 as shown in FIG. 7 using attachment mechanism 140 (or attachment mechanism 340) (steps 705 and 706). The combination of underwear 700, liner 600, and shield 100 or shield 300 can then be worn by a woman. After use, liner 600 can be removed (step 707) a new liner 600 inserted as described previously (step 708) and then old liner 600 can be washed (step 709). Thereafter, old liner 600 can be reused.

Figure 8:
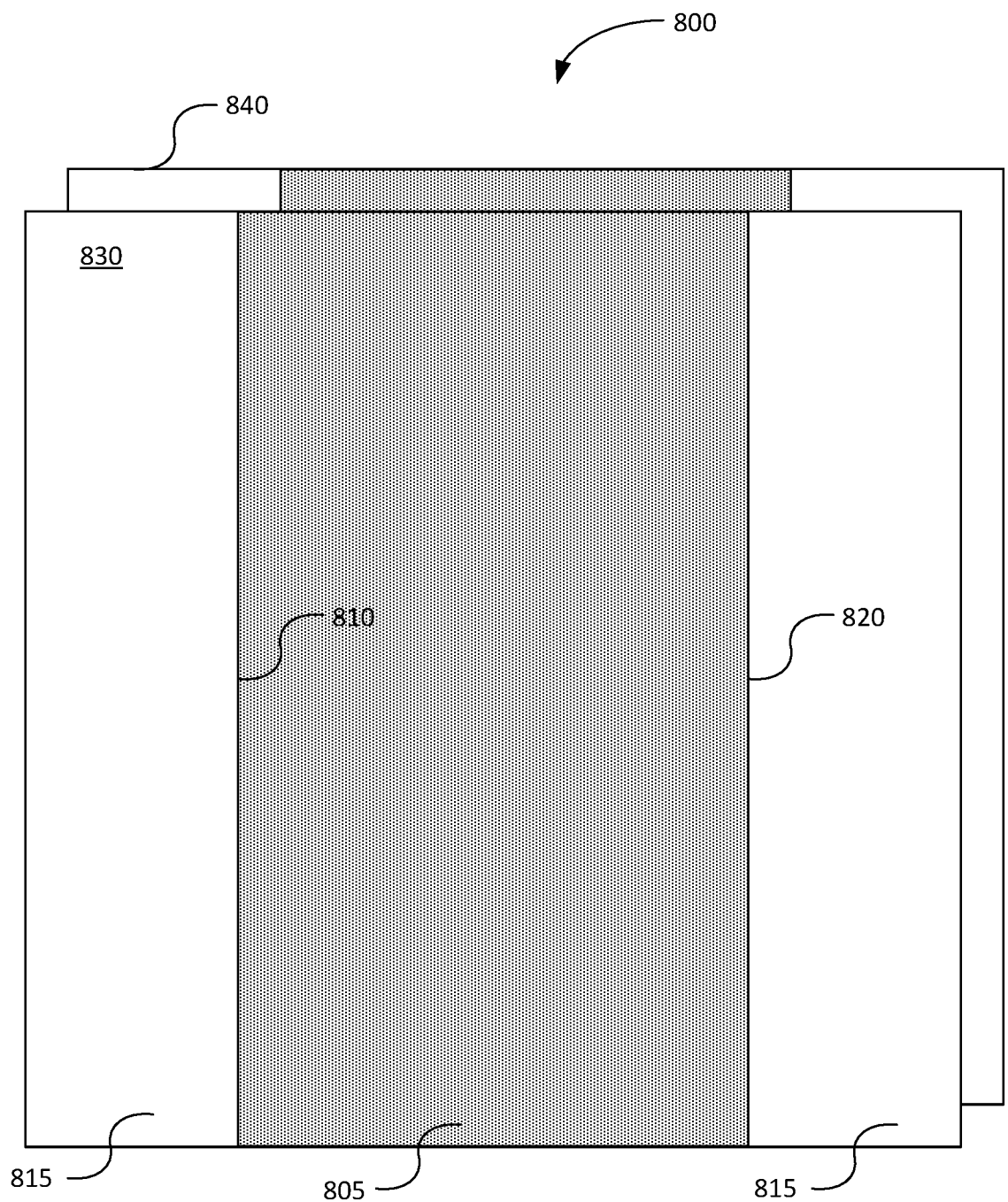
FIG. 8 depicts an improved alternative embodiment of a reusable liner shown in FIG. 5.

FIG. 8 depicts an alternative embodiment of a liner 800. Liner 800 is an improved alternative over liner 500. In the preferred embodiments, liner 800 has two or more layers (e.g., first layer 830 and second layer 840). In some embodiments, first layer 830 and second layer 840 are made from cloth, preferably cotton or flannel. In some embodiments, first layer 830 and second layer 840 are made from cloth made of absorbent synthetic material. In some embodiments, first layer 830 and second layer 840 are sewn or adhered together or attached using other means.

Referring to FIG. 8, each layer has a center region (e.g., 805 within layer 830 and layer 840) flanked by two side regions 815. In the preferred embodiments, the center region is relatively more absorbent than the flanking side regions 815. In some embodiments, center region 805 is padded with absorbent material (e.g., cotton or synthetic material). In some embodiments, center region 805 is made of a more absorbent material (e.g., flannel, a thicker layer of cotton or synthetic material) relative to the side regions (e.g., cotton). In some embodiments, the center region is made of multiple layers of fabrics while the side regions are made of only one layer. In some embodiments, the center region is made of more layers of fabrics than the side regions. In some embodiments, side regions 815 are rectangular. In some embodiments, side regions 815 have bent or curved end corners. When in use, the layer is folded alone lines 810 and 820. In the embodiments where multiple layers are used, the layers are aligned first and then folder along lines 810 and 820, such that the more absorbent center regions from different layers are stacked right on top of each other.

In some embodiments, a layer in liner 800 (either layer 830, layer 840 or both) is approximately a square as shown in FIG. 8. In some embodiments, a layer in liner 800 (either layer 830, layer 840 or both) is approximately a rectangle. In some embodiments, a layer in liner 800 (either layer 830, layer 840 or both) has curved or bent corners. It will be understood that a layer in liner 800 can have side regions of any reasonable shape or size so long as they provide support or additional absorbance capacity when the liner is assembly and inserted into pockets.

Figure 9A:
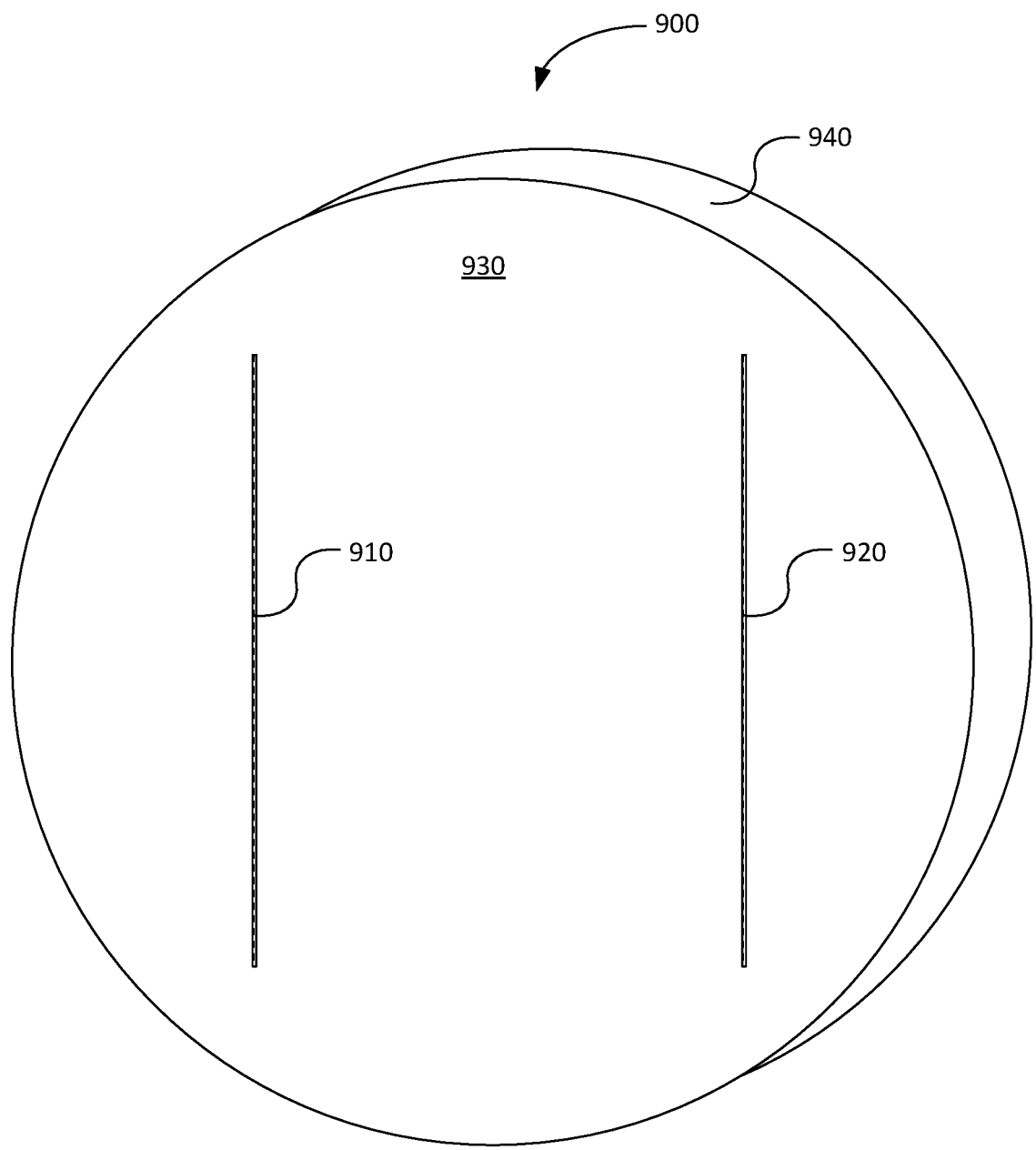
FIG. 9A depicts an alternative embodiment of a reusable liner developed by the applicant.
Figure 9B:
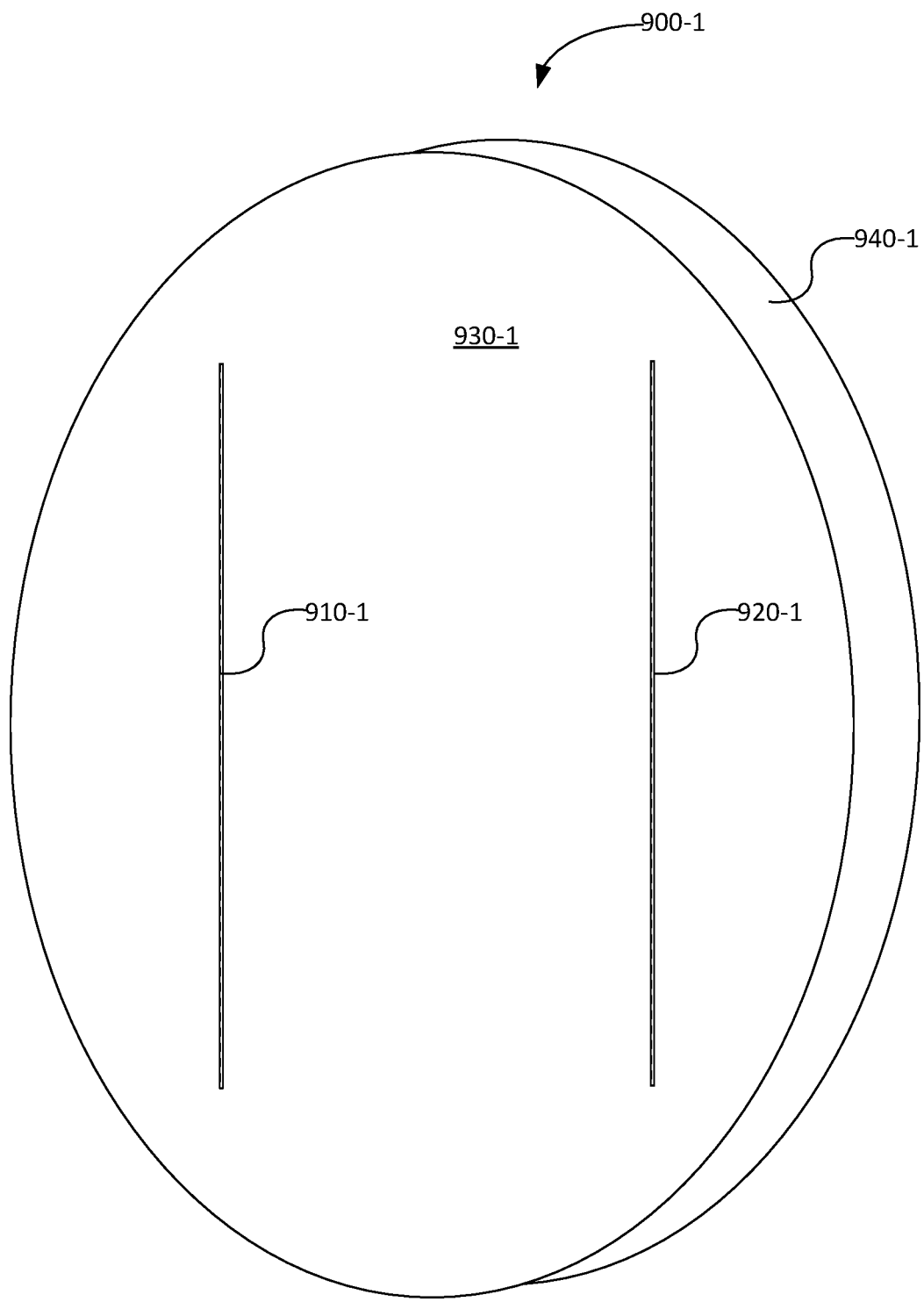
FIG. 9B depicts an alternative embodiment of a reusable liner developed by the applicant.

FIGS. 9A and 9B depict alternative embodiments of a liner 900. In some embodiments, a layer in liner 900 (either first layer 930, second layer 940 or both) is approximately a circle as shown in FIG. 9. In some embodiments, a layer in a liner is approximately an oval; see, for example, layers 930-1 and 940-1 in liner 900-1 depicted in FIG. 9B. It will be understood that a layer can have any side regions on long as they provide support or additional absorbance capacity when the liner is assembly and inserted into pockets. When in use, the layer is folded alone lines 910 and 920 (or 910-1 and 920-1). In the embodiments where multiple layers are used, the layers are aligned first and then folder along lines 910 and 920 (or 910-1 and 920-1).

In some embodiments, liners are made according to one or more predetermined dimensions such that different liners can be used interchangeably. In some embodiments, layers from different liners can be used in a mix and match fashion. For example, exemplary dimensions for square liners depicted in FIG. 8 include but are not limited to 7 inches×7 inches, (7 and ±¼) inches×(7 and ±¼) inches, (7 and ±½) inches×(7 and ±½) inches, 8 inches×8 inches, (8 and ±¼) inches×(8 and ±¼) inches, (8 and ±½) inches×(8 and ±½) inches, 9 inches×9 inches, (9 and ±½) inches×(9 and ±½) inches, (9 and ¼) inches×(9 and ±¼) inches, 10 inches×10 inches, (10 and ±½) inches×(10 and ±½) inches, (10 and ±¼) inches×(10 and ±¼) inches, 11 inches×11 inches, (11 and ±½) inches×(11 and ±½) inches, (11 and ±¼) inches× (11 and ±¼) inches, 12 inches×12 inches, (12 and ±½) inches×(12 and ±½) inches, (12 and ±¼) inches×(12 and ±¼) inches, and etc. It will be understood that these dimensions can vary when the liner design varies. Similar variations in dimension can apply to non-square liners, including but not limited to rectangular, circular, oval liners, and liners of more irregular shapes. For rectangular and oval liners, the dimensions will not be equal in size; for example, length and width of the rectangular and oval liners can vary by 0.5 inch or less, 1 inch or less, 1.5 inches or less, 2 inches or less, 2.5 inches or less, 3 inches or less, or 5 inches or less.

Additionally, the predetermined dimensions of liners can vary depending on the purposes. For example, postpartum liners generally have larger dimensions.

In some embodiments, shields are also made according to one or more predetermined dimensions to accommodate liners of different dimensions. Shields can adopt any dimensions that are suitable for accommodating liners of different dimensions. It would be understood that shields are of slightly larger dimensions when being compared to the liners. In some embodiments, a shield is 0.01 inch or larger, 0.02 inch or larger, 0.05 inch or larger, 0.1 inch or larger, 0.15 inch or larger, 0.2 inch or larger, 0.25 inch or larger, 0.3 inch or larger, 0.4 inch or larger, 0.5 inch or larger, in at least one dimension, when being compared with a liner.

For example, as depicted in FIG. 3, preferred embodiments of regular lines can be around 8.5 inches×around 8.5 inches or around 8.5 inches×around 5.75 inches. Preferred embodiments of postpartum liners can be around 12 inches× around 10.5 inches or around 12 inches×around 7.5 inches. Preferred embodiments of regular shields can be around 9.5 inches×around 7.75 inches while preferred embodiments of postpartum shields can be around 12 inches×7.75 inches.

It will be understood that the dimensions of both liners and shields can also be varied to provide better fit for and comfort to individual women.

The exemplary liners disclosed herein include two layers. However, a single layer may be used at the beginning or end of a menstrual circle. It will be understood by one of skill in the art that any number of layers may be assembled and used to suit a user's need and comfort.

References to the present invention herein are not intended to limit the scope of any claim or claim term, but instead merely make reference to one or more features that may be covered by one or more of the claims. Structures, processes and numerical examples described above are exemplary only, and should not be deemed to limit the claims. It should be noted that, as used herein, the terms "over" and "on" both inclusively include "directly on" (no intermediate materials, elements or space disposed there between) and "indirectly on" (intermediate materials, elements or space disposed there between).

What is claimed is:

1. A reusable liner and shield for use with underwear, comprising:
    a liner comprising one or more layers of absorbent cloth of a predetermined first shape selected from the group consisting of an octagon, a circle, and an oval;
    a shield comprising:
    a first piece;
    a second piece attached to a first side of the first piece to form a first pocket;
    a third piece attached to the first side of the first piece to form a second pocket;
    a fourth piece made of non-absorbent material to stop leakage to the underwear attached to a second side of the first piece; and
    an attachment mechanism for removably attaching the shield to the underwear;
    wherein the one or more layers of absorbent cloth of the liner of the predetermined first shape is folded along a first fold line and a second fold line to form a rectangle and one end of the liner is removably placed in the first pocket and another end of the liner is removably placed in the second pocket.

2. The liner and shield of claim 1, wherein the fourth piece is made of polyurethane laminate.

3. The liner and shield of claim 1, wherein the cloth comprises cotton, flannel, or synthetic material.

4. The liner and shield of claim 3, wherein the first piece, second piece, and third piece each comprise cotton.

5. The liner and shield of claim 1, wherein the shield comprises a fifth piece attached to the fourth piece.

6. The liner and shield of claim 5, wherein the fifth piece comprises cotton.

7. The liner and shield of claim 1, wherein the attachment mechanism comprises one selected from the group consisting of a snap, a button, hook and loop fastener, zipper, and a pair of strings for forming a knot.

8. A method of using a reusable liner and shield, comprising:
    folding an octagonal liner comprised of absorbent cloth along a first fold line;
    folding the octagonal liner along a second fold line to form a rectangle;
    inserting one end of the liner into a first pocket in a shield wherein the shield contains a non-absorbent piece to stop leakage to an undergarment;
    inserting another end of the liner into a second pocket in a shield;
    attaching the shield to the undergarment using an attachment mechanism; and
    removing the liner from the shield.

9. The method of claim 8, wherein the liner comprises a first layer and a second layer.

10. The method of claim 8, wherein said non-absorbent piece of the shield comprises a piece of polyurethane laminate.

11. The method of claim 10, wherein the shield comprises a first piece of cotton attached to a first side of the piece of polyurethane laminate.

12. The method of claim 11, wherein the shield comprises a second piece of cotton attached to a second side of the piece of polyurethane laminate.

13. The method of claim 8, wherein the attachment mechanism comprises one selected from the group consisting of a snap, a button, hook and loop fastener, zipper, and a pair of strings for forming a knot.

14. The method of claim 10, further comprising: washing the liner.

15. The method of claim 14, further comprising: reusing the liner in the shield.

16. A reusable liner and shield for use with underwear, comprising:
- a liner comprising one or more layers of cloth of a non-rectangular shape;
- a shield comprising:
- a first piece;
- a second piece attached to a first side of the first piece to form a first pocket;
- a third piece attached to the first side of the first piece to form a second pocket;
- a fourth piece comprised of non-absorbent material to stop leakage to the underwear attached to a second side of the first piece; and
- an attachment mechanism for removably attaching the shield to the underwear;
- wherein the one or more layers of cloth of the liner of a non-rectangular shape is folded along a first fold line and a second fold line to form a rectangle and a first end of the liner is removably placed in the first pocket and a second end of the liner is removably placed in the second pocket, the liner comprising a greater number of layers of cloth in the center of the rectangle than near the first end and near the second end.

17. The reusable liner and shield of claim 16, wherein at least one of the one or more layers is made of cotton, flannel, or a synthetic absorbent material.

* * * * *